United States Patent
Marat

(10) Patent No.: US 11,052,028 B2
(45) Date of Patent: Jul. 6, 2021

(54) PROCESS FOR DEPIGMENTING KERATIN MATERIALS USING THIOPYRIDINONE COMPOUNDS

(71) Applicant: L'OREAL, Paris (FR)

(72) Inventor: Xavier Marat, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/804,531

(22) Filed: Jul. 21, 2015

(65) Prior Publication Data
US 2016/0045420 A1 Feb. 18, 2016

Related U.S. Application Data

(62) Division of application No. 13/994,457, filed as application No. PCT/EP2011/072180 on Dec. 8, 2011, now Pat. No. 9,138,392.

(60) Provisional application No. 61/425,258, filed on Dec. 21, 2010.

(30) Foreign Application Priority Data

Dec. 14, 2010 (FR) ...................... 10 60474

(51) Int. Cl.
*A61K 8/49* (2006.01)
*A61Q 19/02* (2006.01)
*C07D 213/82* (2006.01)

(52) U.S. Cl.
CPC .......... *A61K 8/4926* (2013.01); *A61K 8/4933* (2013.01); *A61Q 19/02* (2013.01); *C07D 213/82* (2013.01)

(58) Field of Classification Search
None
See application file for complete search history.

(56) References Cited

U.S. PATENT DOCUMENTS

| 4,548,942 A | 10/1985 | Shroot et al. |
| 5,476,852 A * | 12/1995 | Cauwenbergh .......... A61K 8/49 514/254.07 |
| 2004/0110721 A1* | 6/2004 | Zeng ................. A61K 31/4178 514/53 |

FOREIGN PATENT DOCUMENTS

| FR | 2 555 450 | 5/1985 |
| JP | 5 124924 | 5/1993 |

OTHER PUBLICATIONS

Pregnolato et al. II Farmaco, vol. 55, pp. 669-679. publication year: 2000.*
Office Action in Japanese Patent Application No. 2013-543653, dated Aug. 3, 2015.
"3-Pyridinecarboxamide, 1, 2-dihydro-N-(2-hydroxy-4-methylphenyl)-2-thioxo-", retrieved from STN Database accession No. 1061764-16-6, Database Registry (Online) Chemical Abstracts Service, Database: ChemSpider (ChemZoo, Inc.) , Total pp. 1, (Oct. 15, 2009), XP 002672457.
"3-Pyridinecarboxamide, N-cycloheptyl-1-1, 2-dihydro-2-thioxo-", Database Registry (Online), Chemical Abstracts Service, Chemical Library, Database accession No. 451473-73-7, Total p. 1, (Sep. 16, 2002), XP 002672458.
International Search Report dated Apr. 16, 2012 in PCT/EP11/72180 Filed Dec. 8, 2011.
Pagani et al. J. Med. Chem vol. 43, pp. 199-204; publication year: 2000.
eMedicine. Propionibacterium Infections [online]. eMedicine, 2008. [retrieved on: Nov. 17, 2014]. retrieved from the internet <http://emedicine. medscape.com/article/226337 -overview>.
Office Action dated Nov. 14, 2016 in Japanese Patent Application No. 2015-231634 (submitting English translation only).

* cited by examiner

Primary Examiner — Katherine Peebles
(74) Attorney, Agent, or Firm — Oblon, McClelland, Maier & Neustadt, L.L.P.

(57) ABSTRACT

The invention relates to cosmetic processes and compositions for depigmenting, lightening and/or whitening keratin materials, in particular the skin, which comprises the application of a cosmetic composition comprising thiopyridinone compounds to keratin materials.

20 Claims, No Drawings

PROCESS FOR DEPIGMENTING KERATIN MATERIALS USING THIOPYRIDINONE COMPOUNDS

This application is a Divisional of U.S. application Ser. No. 13/994,457, filed on Aug. 8, 2013, allowed, which is a National Stage of application PCT/EP11/072180, filed on Dec. 8, 2011, which claims benefit of Provisional Application Ser. No. 61/425,258, filed on Dec. 21, 2010.

The present invention relates to a cosmetic treatment process in particular for depigmenting and/or whitening the skin, that employs at least one compound of thiopyridinone type.

At various periods in their life, certain people develop darker and/or more coloured marks on their skin, and more especially on the hands, which gives the skin a heterogeneous appearance. These marks are due in particular to a high concentration of melanin in the keratinocytes located at the surface of the skin.

The use of harmless topical depigmenting substances which exhibit good efficacy is especially desirable with a view to treating pigmentary marks.

The mechanism of formation of skin pigmentation, i.e. of the formation of melanin, is particularly complex and involves, schematically, the following principal steps:

Tyrosine-→Dopa-→Dopaquinone-→Dopachrome-→Melanin

Tyrosinase (monophenol dihydroxyl phenylalanine: oxygen oxidoreductase EC 1.14.18.1) is the essential enzyme involved in this series of reactions. It catalyzes in particular the reaction converting tyrosine to Dopa (dihydroxyphenylalanine) by virtue of its hydroxylase activity, and the reaction converting Dopa to dopaquinone by virtue of its oxidase activity. This tyrosinase acts only when it is in the mature form, under the action of certain biological factors.

A substance is acknowledged to be depigmenting if it acts directly on the vitality of epidermal melanocytes, where melanogenesis takes place, and/or if it interferes with one of the steps of melanin biosynthesis, either by inhibiting one of the enzymes involved in melanogenesis, or by being inserted as a structural analogue of one of the chemical compounds of the melanin synthesis chain, which chain may then be blocked and thus ensure depigmentation.

Arbutin, niacinamide and kojic acid are known as skin depigmenting agents.

Substances have been sought which exhibit an effective depigmenting action, in particular greater than that of arbutin, niacinamide and kojic acid.

In this regard, the applicant has found, surprisingly and unexpectedly, that certain thiopyridinone compounds exhibit good depigmenting activity, even at low concentration.

The subject of the invention is therefore a nontherapeutic cosmetic process for depigmenting, lightening and/or whitening keratin materials, in particular the skin, which comprises the application of a cosmetic composition comprising, in a physiologically acceptable medium, at least one compound of formula (I) as defined hereinafter.

The invention also relates to the nontherapeutic cosmetic use of a compound of formula (I) as a whitening, lightening and/or depigmenting agent for keratin materials, in particular the skin.

The compounds used according to the invention allow effective depigmenting and/or lightening, or even whitening, of the skin of human beings. They are in particular intended to be applied to the skin of individuals exhibiting brownish pigmentation marks or senescence marks, or to the skin of individuals who wish to combat the appearance of a brownish colour arising from melanogenesis.

They may also allow depigmentation and/or lightening of body hair, the eyelashes, head hair and also the lips and/or the nails.

The compounds used according to the invention therefore correspond to formula (I) or (I') below:

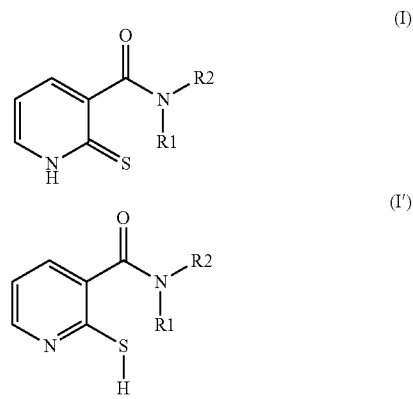

in which:

$R_1$ and $R_2$, which may be identical or different, denote a radical chosen from:
a) a hydrogen atom;
b) a saturated linear $C_1$-$C_{20}$ or branched $C_3$-$C_{20}$ or unsaturated $C_2$-$C_{20}$ alkyl group, optionally interrupted with one or more heteroatoms chosen from N, S and O, and/or optionally substituted with one or more groups, which may be identical or different, chosen from:
   i) —$OR_3$
   ii) —$SR_3$,
   iii) —$NR_3R_4$
   iv) —$CONHR_3$
   v) —$COOR_3$;
   vi) a $C_5$-$C_{12}$ aryl group optionally substituted with one or more hydroxyls and/or with one or more $C_1$-$C_8$ alkoxy radicals;
c) a saturated $C_1$-$C_8$ alkyl group substituted with a $C_5$-$C_{12}$ aryl radical optionally substituted with one or more hydroxyls and/or with one or more $C_1$-$C_8$ alkoxy radicals;
d) a phenyl group optionally substituted with one or more hydroxyls and/or with one or more $C_1$-$C_8$ alkoxy radicals;

$R_3$ denoting a hydrogen atom or a saturated linear $C_1$-$C_5$ or branched $C_3$-$C_5$ or unsaturated $C_2$-$C_5$ hydrocarbon-based group, $R_4$ denoting a hydrogen atom; a saturated linear $C_1$-$C_5$ or branched $C_3$-$C_5$ hydrocarbon-based group; or an acetyl group;

it being possible for $R_1$ and $R_2$ to form, with the nitrogen atom which bears them, a ring chosen from pyrrolidine, pyrroline, piperidine, piperazine, morpholine, thiomorpholine and azepine;

and also the salts thereof, the solvates thereof and the optical isomers thereof, and the racemates thereof.

The compound (I') is the tautomer form of the compound (I) when a tautomeric equilibrium exists according to the following scheme:

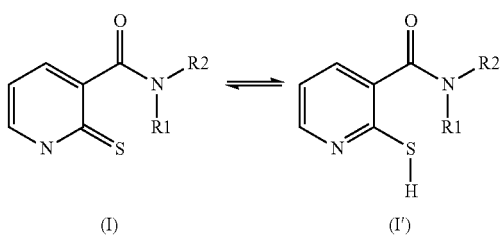

The salts of the compounds of formula (I) or (I') comprise the conventional nontoxic salts of said compounds, such as those formed from acid or from base.

As salts of the compound of formula (I) or (I'), when it comprises a quaternizable nitrogen atom), mention may be made of:

a) the salts obtained by addition of the compound (I) or (I') with an inorganic acid, in particular chosen from hydrochloric acid, boric acid, hydrobromic acid, hydrioic acid, sulphuric acid, nitric acid, carbonic acid, phosphoric acid and tetrafluoroboric acid;

b) or the salts obtained by addition of the compound (I) or (I') with an organic acid, in particular chosen from acetic acid, propionic acid, succinic acid, fumaric acid, lactic acid, glycolic acid, citric acid, gluconic acid, salicylic acid, tartaric acid, terephthalic acid, methylsulphonic acid, ethylsulphonic acid, benzenesulphonic acid, toluenesulphonic acid and triflic acid.

Mention may also be made of the salts obtained by addition of the compound of formula (I) or (I') (when it comprises an acid group) with an inorganic base, such as sodium hydroxide, potassium hydroxide, calcium hydroxide, ammonium hydroxide, magnesium hydroxide, lithium hydroxide, and sodium, potassium or calcium carbonates or hydrogen carbonates, for example;

or with an organic base, such as a primary, secondary or tertiary alkylamine, for example triethylamine or butylamine. This primary, secondary or tertiary alkylamine may comprise one or more nitrogen and/or oxygen atoms and may therefore comprise, for example, one or more alcohol functions; mention may in particular be made of 2-amino-2-methylpropanol, ethanolamine, triethanolamine, 2-dimethylaminopropanol, 2-amino-2-(hydroxymethyl)-1,3-propanediol and 3-(dimethylamino)propylamine.

Mention may also be made of amino acids such as, for example, lysine, arginine, guanidine, glutamic acid or aspartic acid.

Advantageously, the salts of the compounds of formula (I) or (I') (when it comprises an acid group) may be chosen from alkali metal salts or alkaline earth metal salts, such as sodium, potassium, calcium or magnesium salts; and ammonium salts.

Advantageously, the salts of the compounds of formula (I) or (I') (when it comprises a quaternizable nitrogen atom) can be chosen from halides such as chloride or bromide; and citrates, acetates, succinates, phosphates, lactates and tartrates.

The acceptable solvates of the compounds described in the present invention comprise conventional solvates such as those formed during the preparation of said compounds as a result of the presence of solvents. By way of example, mention may be made of the solvates resulting from the presence of water or of linear or branched alcohols such as ethanol or isopropanol.

The optical isomers are in particular enantiomers and diastereoisomers.

Preferentially, the linear or branched groups can be chosen from: methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl.

More preferentially, the saturated linear or branched alkyl groups can be chosen from methyl, ethyl, propyl, isopropyl, butyl, isobutyl, tert-butyl, pentyl, hexyl, heptyl and octyl.

Preferentially, the $C_1$-$C_4$ alkoxy groups can be chosen from methoxy, ethoxy, propoxy and butoxy, and even more preferentially methoxy.

The compounds of formula (I) can be obtained, in a known manner, by reacting 2-mercaptonicotinic acid and an amine of formula $HNR_1R_2$ ($R_1$ and $R_2$ having the meanings described above), in particular in the presence of a base such as carbonyldiimidazole.

The compounds of formula (I) can also be obtained, in a known manner, by reacting 2-mercaptonicotinic acid or 2-chloronicotinic acid with an amine of formula $HNR_1R_2$ ($R_1$ and $R_2$ having the meanings described above), in particular in the presence of an agent for activating carboxylic acids according to the conventional methods for activating acids (described, for example, in Comprehensive Organic Transformation, published by Wiley VCH, in the chapter Interconversion of nitriles, carboxylic acids and derivatives). Use is preferably made of an agent for activating carboxylic acids which makes it possible to form an acid chloride (for example, using thionyl chloride or oxalyl chloride, or 1-chloro-N,N,2-trimethyl-1-propenamine) or to form a mixed anhydride (using alkyl chloroformates), or carbodiimides or diethyl cyanophosphate are used to form carbamimidates or acylphosphonates (Phosphorus in organic synthesis-XI, Amino acids and peptides-XXI, Reaction of diethyl phosphorocyanidate with carboxylic acids. A new synthesis of carboxylic esters and amides, Tetrahedron, 32, 1976, 2211-2217).

When 2-chloronicotinic acid is used as starting reagent, the chloroamide obtained is then used in an exchange reaction between chlorine and sulphur by means of reagents such as NaSH, thiourea, sodium thiosulphate or thioacetic acid (in basic medium).

Compounds of formula (I) or (I') are described in the following documents:
EP-A-298752, WO03/014062, EP-A-298752, FR-A-2349591, EP-A-2555450, WO 03/014062 and WO 2008/012532, and in the publications article A. Monge, V. Martinez-Merino; Synthesis of 2-substituted 3-Oxoisothiazolo[5,4-b]pyridines; J. heterocyclic. Chem, 22, 1353 (1985).

article A. Dunn, R. Norrie; Synthesis of pyrido-1,3-thiazines; Zeitschrift fur chemie 1988, vol 28, n° 6, p 212/214.

S. Andreae; J. Parkt. Chem. 339 (1997) 152-158;

S. Gorsuch; Biorganic & Medicinal Chemistry 17(2009) 467-474.

A. Monge et al; J. Heterocyclic Che. 25, 23 (1988).

M. Pregnolato; II Farmaco 55 (2000) 669-679.

Preferably, the compounds of the formula (I) or (I') have the following meanings:

$R_1$ denotes a radical chosen from:

a) a hydrogen atom;

b) a saturated linear $C_1$-$C_{10}$ or branched $C_3$-$C_{10}$ or unsaturated $C_2$-$C_{10}$ alkyl group, optionally substituted with one or more $OR_3$ groups;

$R_2$ denotes a radical chosen from:

a) a saturated linear $C_1$-$C_{10}$ or branched $C_3$-$C_{10}$ or cyclic $C_3$-$C_7$ alkyl group, optionally interrupted with one or more oxygen atoms, preferably one, and/or optionally containing one or more groups, which may be identical or different, chosen from:
i) —$OR_3$,
ii) —$NR_3R_4$,
iii) —$CONHR_3$,
iv) —$COOR_3$ b) a phenyl group optionally substituted with one or more hydroxyls and/or with one or more $C_1$-$C_3$ alkoxy radicals;

c) a saturated $C_1$-$C_5$ alkyl group substituted with a phenyl radical optionally substituted with one or more hydroxyls or with one or more $C_1$-$C_3$ alkoxy radicals;

$R_3$ denoting a hydrogen atom or a saturated linear $C_1$-$C_5$ or branched $C_3$-$C_5$ hydrocarbon-based group;

$R_4$ denoting a hydrogen atom or a saturated linear $C_1$-$C_5$ or branched $C_3$-$C_5$ hydrocarbon-based group;

and the salts thereof, the solvates thereof and the optical isomers thereof, and the racemates thereof.

Preferentially, the compounds of formula (I) or (I') have the following meanings:

$R_1$ denotes a hydrogen atom or a linear $C_1$-$C_4$ alkyl radical optionally substituted with one or more hydroxyl groups;

$R_2$ denotes a radical chosen from:

a) a saturated linear $C_1$-$C_{10}$ or branched $C_3$-$C_{10}$ or cyclic $C_5$-$C_7$ alkyl group, optionally interrupted with an oxygen atom and/or optionally containing a —$CONH_2$ group and/or optionally substituted with one or more hydroxyl groups;

b) a phenyl group;

c) a saturated $C_1$-$C_5$ alkyl group substituted with a phenyl radical optionally substituted with one or more hydroxyl or $C_1$-$C_3$ alkoxy radicals;

and also the salts thereof, the solvates thereof and the optical isomers thereof, and the racemates thereof.

More preferentially, the compounds of formula (I) or (I') have the following meanings:

$R_1$ denotes a hydrogen atom or a $C_1$-$C_4$ hydroxyalkyl group;

$R_2$ denotes a saturated linear $C_1$-$C_{10}$ or branched $C_3$-$C_{10}$ or cyclic $C_5$-$C_6$ alkyl hydrocarbon-based group, optionally interrupted with an oxygen atom and/or optionally containing a —$CONH_2$ group and/or optionally substituted with a hydroxyl group; a phenyl group; or a saturated $C_1$-$C_5$ alkyl group substituted with a phenyl radical itself optionally substituted with one or more hydroxyl or $C_1$-$C_3$ alkoxy radicals;

and also the salts thereof, the solvates thereof and the optical isomers thereof, and the racemates thereof.

The subject of the invention is also the novel compounds of formulae (Ia) and (Ia') corresponding to those of formula (I) or (I')

in which:
when R1 denotes a hydrogen atom, then R2 denotes a radical chosen from unsaturated $C_2$-$C_{20}$ alkyls, cyclic $C_7$ alkyl radicals, saturated linear $C_1$-$C_{20}$ or branched $C_3$-$C_{20}$ alkyls, substituted with one or more identical or different —$OR_3$ groups, and ($C_1$-$C_{20}$)alkylaryls substituted with one or more identical or different —$OR_3$ groups, $R_3$ denoting a hydrogen atom or a saturated linear $C_1$-$C_5$ or branched $C_3$-$C_5$ or unsaturated $C_2$-$C_5$ hydrocarbon-based group;

when $R_1$ denotes a saturated linear $C_1$-$C_{10}$ or branched $C_3$-$C_{10}$ or unsaturated $C_2$-$C_{10}$ alkyl group, optionally substituted with one or more —$OR_3$ groups, then $R_2$ de-notes a radical chosen from:

a) a saturated branched $C_3$-$C_{12}$ or cyclic $C_3$-$C_7$ alkyl group, optionally interrupted with one or more oxygen atoms, preferably one, and/or optionally containing one or more identical or different —$OR_3$ groups, $R_3$ denoting a hydrogen atom or an optionally hydroxylated, saturated linear $C_1$-$C_5$ or branched $C_3$-$C_5$ hydrocarbon-based group;

and also the salts thereof, the optical isomers thereof and the racemates thereof.

Preferably, for the novel compounds of the formulae (Ia) and (Ia'):

when R1 denotes a hydrogen atom, then R2 denotes a radical chosen from unsaturated $C_2$-$C_{20}$ alkyls, saturated linear $C_1$-$C_{20}$ or branched $C_3$-$C_{20}$ alkyls, substituted with one or more identical or different —$OR_3$ groups, and ($C_1$-$C_6$)alkylphenyls substituted with one or more identical or different —$OR_3$ groups, $R_3$ denoting a hydrogen atom or a saturated linear $C_1$-$C_5$ or branched $C_3$-$C_5$ or unsaturated $C_2$-$C_5$ hydrocarbon-based group;

when R1 denotes a saturated linear $C_1$-$C_{12}$ or branched $C_3$-$C_{10}$ or unsaturated $C_2$-$C_{10}$ alkyl group, optionally substituted with one or more —$OR_3$ groups, then $R_2$ de-notes a radical chosen from:

a) a saturated branched $C_3$-$C_{12}$ or cyclic $C_3$-$C_7$ alkyl group, optionally interrupted with one or more oxygen atoms, preferably one, and/or optionally containing one or more identical or different —$OR_3$ groups, $R_3$ denoting a hydrogen atom or an optionally hydroxylated, saturated linear $C_1$-$C_5$ or branched $C_3$-$C_5$ hydrocarbon-based group, and also the salts thereof, the optical isomers thereof and the racemates thereof.

Preferably, for the novel compounds of formulae (Ia) and (Ia'):

when $R_1$ denotes a hydrogen atom, then $R_2$ denotes a radical chosen from saturated linear $C_1$-$C_{20}$ or branched $C_3$-$C_{20}$ alkyls, substituted with one or more identical or different —$OR_3$ groups, and ($C_1$-$C_6$)alkylphenyls substituted with one or more identical or different —$OR_3$ groups, $R_3$ denoting a hydrogen atom or a saturated linear $C_1$-$C_5$ or branched $C_3$-$C_5$ or unsaturated $C_2$-$C_5$ hydrocarbon-based group;

when $R_1$ denotes a saturated linear $C_1$-$C_{10}$ or branched $C_3$-$C_{10}$ or unsaturated $C_2$-$C_{10}$ alkyl group, optionally substituted with one or more —$OR_3$ groups, then $R_2$ de-notes a radical chosen from:

a) a saturated branched $C_3$-$C_{12}$ or cyclic $C_3$-$C_7$ alkyl group, optionally interrupted with one or more oxygen atoms, preferably one, and/or optionally containing one or more identical or different —$OR_3$ groups, $R_3$ denoting a hydrogen atom or an optionally hydroxylated, saturated linear $C_1$-$C_5$ or branched $C_3$-$C_5$ hydrocarbon-based group.

Preferably, for the novel compounds of formulae (Ia) and (Ia'):

$R_1$ denotes a hydrogen atom and $R_2$ denotes a radical chosen from:

a) a saturated linear $C_1$-$C_{10}$ or branched $C_3$-$C_{10}$ or cyclic $C_5$-$C_7$ alkyl group, substituted with one or more hydroxyl groups, and optionally interrupted with an oxygen atom, or $R_1$ denotes a linear $C_1$-$C_4$ alkyl radical optionally substituted with one or more hydroxyl groups; and $R_2$ denotes a radical chosen from:

a) a saturated linear $C_1$-$C_{10}$ or branched $C_3$-$C_{10}$ or cyclic $C_5$-$C_7$ alkyl group, substituted with one or more hydroxyl groups, and optionally interrupted with an oxygen atom.

Preferentially, for the novel compounds of formulae (Ia) and (Ia'):

$R_1$ denotes a hydrogen atom and $R_2$ denotes a saturated linear $C_1$-$C_{10}$ or branched $C_3$-$C_{10}$ or cyclic $C_5$-$C_6$ alkyl hydrocarbon-based group, optionally interrupted with an oxygen atom and optionally substituted with a hydroxyl group, or $R_1$ denotes a $C_1$-$C_4$ hydroxyalkyl group;

$R_2$ denotes a saturated linear $C_1$-$C_{10}$ or branched $C_3$-$C_{10}$ or cyclic $C_5$-$C_6$ alkyl hydrocarbon-based group, optionally interrupted with an oxygen atom and optionally substituted with a hydroxyl group.

Among the compounds of formula (I), the following compounds are preferably used:

| No. | Structure | Chemical name | CAS No. |
|---|---|---|---|
| 1 | 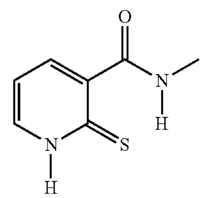 | N-methyl-2-thioxo-1,2-dihydropyridine-3-carboxamide | 91859-74-4 |
| 2 | 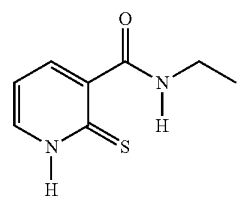 | N-ethyl-2-thioxo-1,2-dihydropyridine-3-carboxamide | 91859-75-5 |
| 3 | 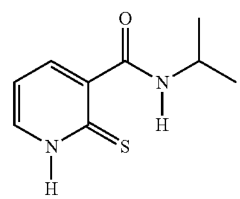 | N-isopropyl-2-thioxo-1,2-dihydropyridine-3-carboxamide | 91859-76-6 |
| 4 | 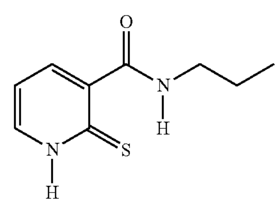 | N-propyl-2-thioxo-1,2-dihydropyridine-3-carboxamide | 330667-56-6 |
| 5 | 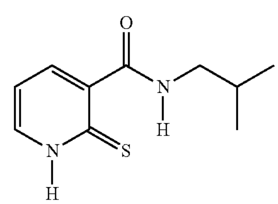 | N-(2-methylpropyl)-2-thioxo-1,2-dihydropyridine-3-carboxamide | 1100027-79-9 |
| 6 | 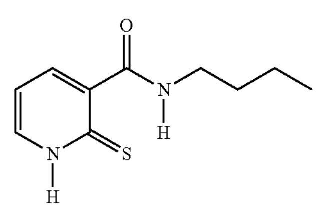 | N-butyl-2-thioxo-1,2-dihydropyridine-3-carboxamide | 65282-55-5 |
| 7 | 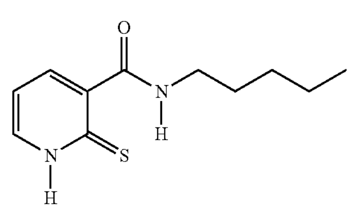 | N-pentyl-2-thioxo-1,2-dihydropyridine-3-carboxamide | 330667-57-7 |

-continued

| No. | Structure | Chemical name | CAS No. |
|---|---|---|---|
| 8 | 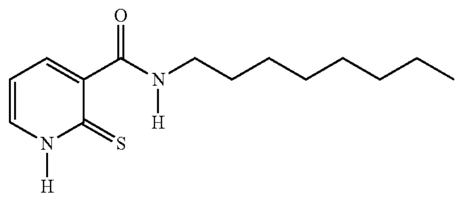 [SMILES: CCCCCCCCNC(=O)c1ccc[nH]c1=S] | N-octyl-2-thioxo-1,2-dihydropyridine-3-carboxamide | 91859-77-7 |
| 9 | 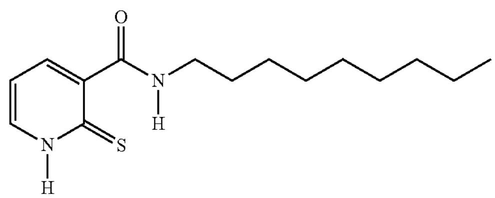 [SMILES: CCCCCCCCCNC(=O)c1ccc[nH]c1=S] | N-nonyl-2-thioxo-1,2-dihydropyridine-3-carboxamide | 1031149-44-6 |
| 10 | 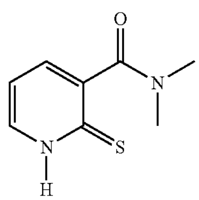 | N,N-dimethyl-2-mercaptonicotinamide | 121650-19-9 |
| 11 | 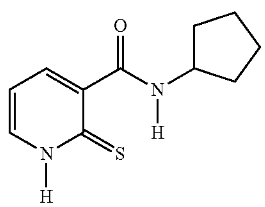 [SMILES: O=C(NC1CCCC1)c1ccc[nH]c1=S] | N-cyclopentyl-2-thioxo-1,2-dihydropyridine-3-carboxamide | 1099928-42-3 |
| 12 | 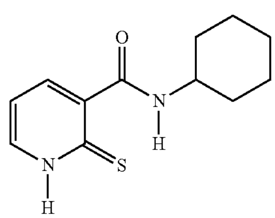 [SMILES: O=C(NC1CCCCC1)c1ccc[nH]c1=S] | N-cyclohexyl-2-thioxo-1,2-dihydropyridine-3-carboxamide | 91859-78-8 |
| 13 | 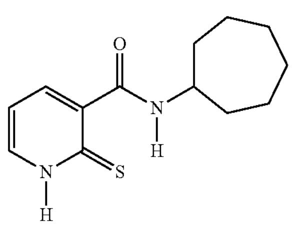 [SMILES: O=C(NC1CCCCCC1)c1ccc[nH]c1=S] | N-cycloheptyl-2-thioxo-1,2-dihydropyridine-3-carboxamide | 451473-73-7 |
| 14 | 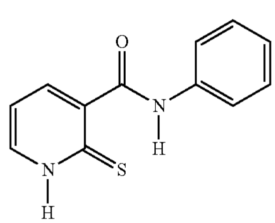 [SMILES: O=C(Nc1ccccc1)c1ccc[nH]c1=S] | N-phenyl-2-thioxo-1,2-dihydropyridine-3-carboxamide | 104857-16-1 |

-continued

| No. | Structure | Chemical name | CAS No. |
|---|---|---|---|
| 15 | 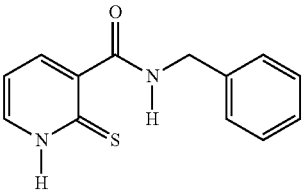 [SMILES: O=C(NCc1ccccc1)c1ccc[nH]c1=S] | N-benzyl-2-thioxo-1,2-dihydropyridine-3-carboxamide | 91859-79-9 |
| 16 | 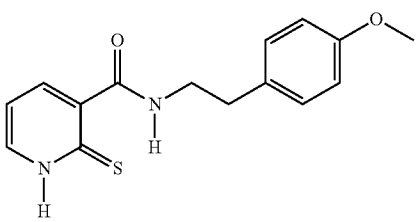 [SMILES: COc1ccc(CCNC(=O)c2ccc[nH]c2=S)cc1] | N-[2-(4-methoxyphenyl)ethyl]-2-thioxo-1,2-dihydropyridine-3-carboxamide | 923682-88-6 |
| 17 | 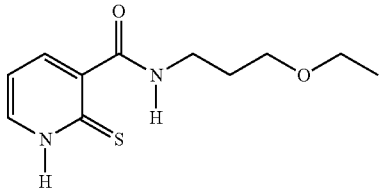 [SMILES: CCOCCCNC(=O)c1ccc[nH]c1=S] | N-(3-ethoxypropyl)-2-thioxo-1,2-dihydropyridine-3-carboxamide | 1061763-97-02 |
| 18 | 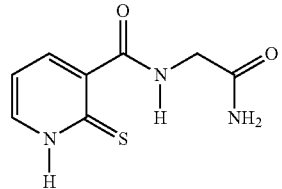 [SMILES: NC(=O)CNC(=O)c1ccc[nH]c1=S] | N-(2-amino-2-oxoethyl)-2-thioxo-1,2-dihydropyridine-3-carboxamide | 497262-18-7 |
| 19 | 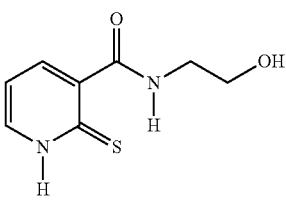 [SMILES: O=C(NCCO)c1ccc[nH]c1=S] | N-(2-hydroxyethyl)-2-thioxo-1,2-dihydropyridine-3-carboxamide | |
| 20 | 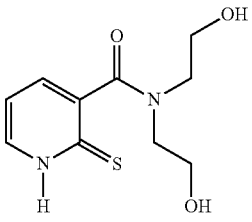 [SMILES: O=C(c1ccc[nH]c1=S)N(CCO)CCO] | N,N-bis(2-hydroxyethyl)-2-thioxo-1,2-dihydropyridine-3-carboxamide | |
| 21 | 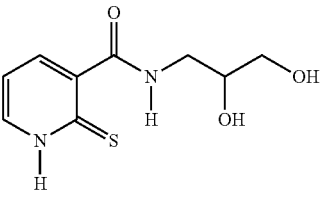 [SMILES: O=C(NCC(O)CO)c1ccc[nH]c1=S] | N-(2,3-dihydroxypropyl)-2-thioxo-1,2-dihydropyridine-3-carboxamide | |

-continued

| No. | Structure | Chemical name | CAS No. |
|---|---|---|---|
| 22 | 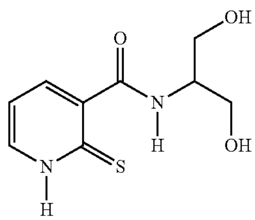 [SMILES: O=C(NC(CO)CO)c1ccc[nH]c1=S] | N-(1,3-dihydroxypropan-2-yl)-2-thioxo-1,2-dihydropyridine-3-carboxamide | |
| 23 | 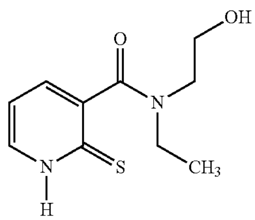 | N-ethyl-N-(2-hydroxyethyl)-2-thioxo-1,2-dihydropyridine-3-carboxamide | |
| 24 | 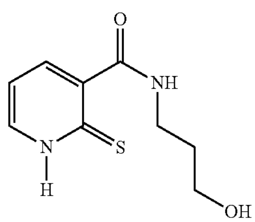 [SMILES: O=C(NCCCO)c1ccc[nH]c1=S] | N-(3-hydroxypropyl)-2-thioxo-1,2-dihydropyridine-3-carboxamide | |
| 25 | 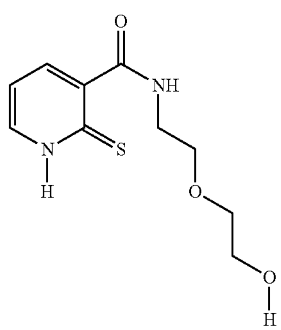 [SMILES: O=C(NCCOCCO)c1ccc[nH]c1=S] | N-[2-(2-hydroxyethoxy)ethyl]-2-thioxo-1,2-dihydropyridine-3-carboxamide | |
| 26 | 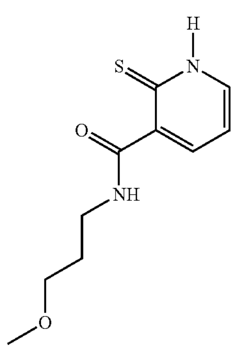 | N-(3-methoxypropyl)-2-thioxo-1,2-dihydropyridine-3-carboxamide | |
| 27 | 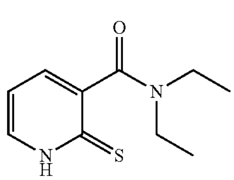 | N,N-diethyl 2-mercaptonicotinamide | 121050-20-2 |

-continued

| No. | Structure | Chemical name | CAS No. |
|---|---|---|---|
| 28 | 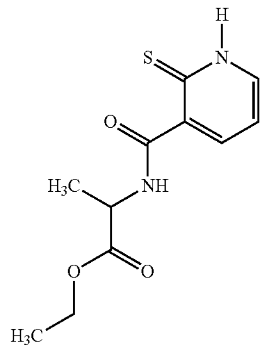 [SMILES: CCOC(=O)C(C)NC(=O)c1ccc[nH]c1=S] | Ethyl N-[(2-thioxo-1,2-dihydropyridin-3-yl)carbonyl]alaninate | |
| 29 | 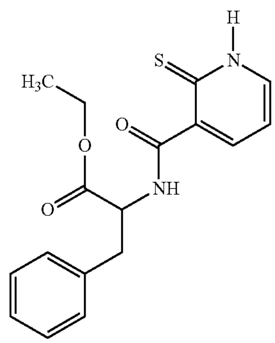 [SMILES: CCOC(=O)C(Cc1ccccc1)NC(=O)c1ccc[nH]c1=S] | Ethyl N-[(2-thioxo-1,2-dihydropyridin-3-yl)carbonyl] phenylalaninate | |
| 30 | 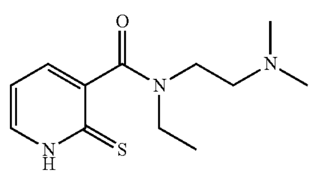 [SMILES: CCN(CCN(C)C)C(=O)c1ccc[nH]c1=S] | N-[2-(dimethylamino)ethyl]-N-ethyl-2-thioxo-1,2-dihydropyridine-3-carboxamide | |

Among these compounds, the following compounds are more particularly preferred:

| No. | Structure | Chemical name |
|---|---|---|
| 1 | | N-methyl-2-thioxo-1,2-dihydropyridine-3-carboxamide |
| 2 | | N-ethyl-2-thioxo-1,2-dihydropyridine-3-carboxamide |
| 3 | 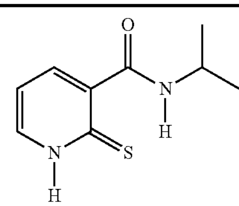 | N-isopropyl-2-thioxo-1,2-dihydropyridine-3-carboxamide |
| 4 | 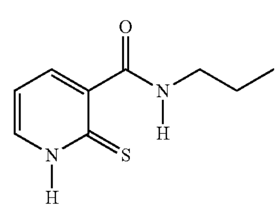 | N-propyl-2-thioxo-1,2-dihydropyridine-3-carboxamide |
| 5 | 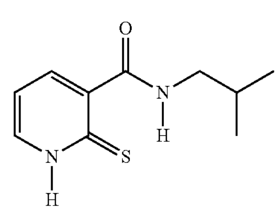 | N-(2-methylpropyl)-2-thioxo-1,2-dihydropyridine-3-carboxamide |

| No. | Structure | Chemical name |
|---|---|---|
| 6 | 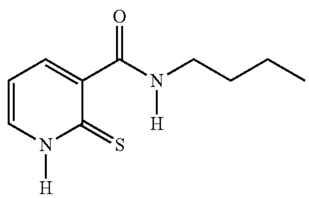 | N-butyl-2-thioxo-1,2-dihydropyridine-3-carboxamide |
| 7 | 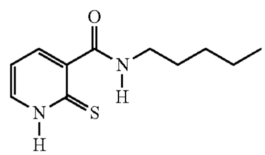 | N-pentyl-2-thioxo-1,2-dihydropyridine-3-carboxamide |
| 11 | 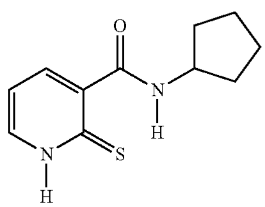 [SMILES: O=C(NC1CCCC1)c1ccc[nH]c1=S] | N-cyclopentyl-2-thioxo-1,2-dihydropyridine-3-carboxamide |
| 12 | 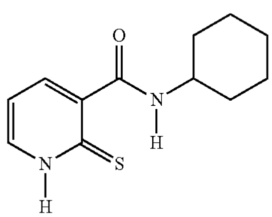 [SMILES: O=C(NC1CCCCC1)c1ccc[nH]c1=S] | N-cyclohexyl-2-thioxo-1,2-dihydropyridine-3-carboxamide |
| 13 | 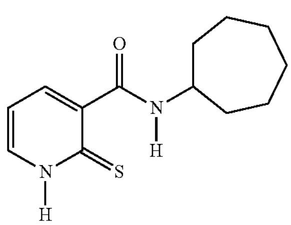 [SMILES: O=C(NC1CCCCCC1)c1ccc[nH]c1=S] | N-cycloheptyl-2-thioxo-1,2-dihydropyridine-3-carboxamide |
| 15 | 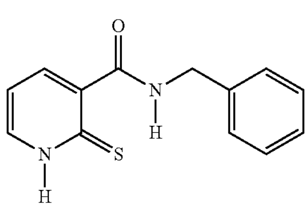 [SMILES: O=C(NCc1ccccc1)c1ccc[nH]c1=S] | N-benzyl-2-thioxo-1,2-dihydropyridine-3-carboxamide |
| 16 | 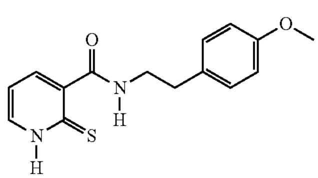 [SMILES: COc1ccc(CCNC(=O)c2ccc[nH]c2=S)cc1] | N-[2-(4-methoxyphenyl)ethyl]-2-thioxo-1,2-dihydropyridine-3-carboxamide |
| 19 | | N-(2-hydroxyethyl)-2-thioxo-1,2-dihydropyridine-3-carboxamide |
| 20 | | N,N-bis(2-hydroxyethyl)-2-thioxo-1,2-dihydropyridine-3-carboxamide |
| 21 | | N-(2,3-dihydroxypropyl)-2-thioxo-1,2-dihydropyridine-3-carboxamide |
| 23 | | N-ethyl-N-(2-hydroxyethyl)-2-thioxo-1,2-dihydropyridine-3-carboxamide |
| 27 | | N,N-diethyl 2-mercaptonicotinamide | and also the salts thereof, the optical isomers thereof and the solvates thereof.

Compounds 1 and 10 are described in application EP-A-298752 as synthesis intermediates.

Compounds 2 to 8, 11 and 12 are described in FR-A-2555450.

Compound 14 is described in the article A. Monge, V. Martinez-Merino; Synthesis of 2-substituted 3-Oxoisothiazolo[5,4-b]pyridines; J. heterocyclic. Chem, 22, 1353 (1985).

Compounds 4, 6, 7 and 15 are described in the article A. Dunn, R. Norrie; Synthesis of pyrido-1,3-thiazines; Zeitschrift fur chemie 1988, vol 28, n° 6, p 212/214.

Compound 14 is described in the article A. Monge, V. Martinez-Merino; Synthesis of 2-substituted 3-Oxoisothiazolo[5,4-b]pyridines; J. heterocyclic. Chem, 22, 1353 (1985).

Compound 18 is described in WO-A-03/014062.
Compound 27 is described in EP 298752.
Compounds 2, 7, 12, 16, 21 and 27 are the most particularly preferred.

The compounds of formula (I) and/or (I') according to the invention are of quite particular use in the cosmetics field.

The composition used according to the invention comprises a compound of formula (I) and/or (I') as described above, in a physiologically acceptable medium.

The compound (I) and/or (I') can be present in the composition used according to the invention in an amount which can be between 0.01 and 10% by weight, preferably between 0.1 and 5% by weight, in particular from 0.5 to 3% by weight, relative to the total weight of the composition.

The term "physiologically acceptable medium" is understood to mean a medium that is compatible with keratin materials of human beings, such as the skin of the body or of the face, the lips, the mucous membranes, the eyelashes, the nails, the scalp and/or the hair.

The composition used according to the invention may thus comprise all the adjuvants which are commonly employed in the cosmetics field.

Mention may in particular be made of: water; organic solvents, in particular $C_2$-$C_6$ alcohols; oils, in particular hydrocarbon-based oils, silicone oils; waxes, pigments, fillers, dyes, surfactants, emulsifiers; cosmetic active agents, UV screens, polymers, thickeners, preservatives, fragrances, bactericides, odour absorbers and antioxidants.

These optional cosmetic adjuvants may be present in the composition in a proportion of from 0.001 to 80% by weight, in particular 0.1 to 40% by weight, relative to the total weight of the composition. In any event, these adjuvants, and also the proportions thereof, will be chosen by those skilled in the art in such a way that the advantageous properties of the compounds according to the invention are not, or not substantially, impaired by the envisaged addition.

As active agents, it will be advantageous to introduce into the composition used according to the invention at least one compound chosen from: desquamating agents; calmatives; organic or inorganic photoprotective agents, moisturizers; depigmenting or propigmenting agents; anti-glycation agents; NO-synthase inhibitors; agents for stimulating the synthesis of dermal or epidermal macromolecules and/or preventing degradation thereof; agents for stimulating fibroblast and/or keratinocyte proliferation or stimulating keratinocyte differentiation; muscle relaxants and/or dermo-decontracting agents; tensioning agents; anti-pollution agents and/or free-radical scavengers; agents that act on the microcirculation; agents that act on the energy metabolism of cells; and mixtures thereof.

Examples of such additional compounds are: retinol and derivatives thereof such as retinyl palmitate; ascorbic acid and derivatives thereof such as magnesium ascorbyl phosphate and ascorbyl glucoside; tocopherol and derivatives thereof such as tocopheryl acetate; nicotinic acid and precursors thereof such as nicotinamide; ubiquinone; glutathione and precursors thereof such as L-2-oxothiazolidine-4-carboxylic acid; plant extracts and in particular plant proteins and hydrolysates thereof, and also plant hormones; marine extracts such as algal extracts; bacterial extracts; sapogenins such as diosgenin and wild yam extracts containing same; ceramides; hydroxy acids such as salicylic acid and 5-n-octanoylsalicylic acid; resveratrol; oligopeptides and pseudodipeptides and acyl derivatives thereof; manganese salts and magnesium salts, in particular the gluconates; and mixtures thereof.

The term "desquamating agent" is intended to mean any compound capable of acting:
either directly on desquamation by promoting exfoliation, such as β-hydroxy acids, in particular salicylic acid and derivatives thereof (including 5-n-octanoylsalicylic acid); α-hydroxy acids, such as glycolic acid, citric acid, lactic acid, tartaric acid, malic acid or mandelic acid; urea; gentisic acid; oligofucoses; cinnamic acid; *Saphora japonica* extract; resveratrol;
or on the enzymes involved in the desquamation or degradation of corneodesmosomes, glycosidases, stratum corneum chymotryptic enzyme (SCCE) or even other proteases (trypsin, chymotrypsin-like). Mention ay be made of agents for chelating mineral salts: EDTA; N-acyl-N,N',N'-ethylenediaminetriacetic acid; aminosulphonic compounds and in particular (N-2 hydroxyethylpiperazine-N-2-ethane)sulphonic acid (HEPES); derivatives of 2-oxothiazolidine-4-carboxylic acid (procysteine); derivatives of alpha-amino acids of glycine type (as described in EP-0 852 949, and also sodium methyl glycine diacetate sold by BASF under the trade name Trilon M); honey; sugar derivatives such as O-octanoyl-6-D-maltose and N-acetylglucosam ine.

The desquamating agents are generally present in the composition according to the invention in proportions ranging from 0.01 to 15% by weight, preferably ranging from 0.1 to 10% by weight, relative to the total weight of the composition.

As calmatives that can be used in the composition according to the invention, mention may be made of: pentacyclic triterpenes and extracts of plants (for example *Glycyrrhiza glabra*) containing them, for instance β-glycyrrhetinic acid and salts and/or derivatives thereof (glycyrrhetinic acid monoglucuronide, stearyl glycyrrhetinate, 3-stearoyloxyglycyrrhetic acid), ursolic acid and salts thereof, oleanolic acid and salts thereof, betulinic acid and salts thereof, an extract of *Paeonia suffruticosa* and/or *lactiflora*, salicylic acid salts and in particular zinc salicylate, phycosaccharides from the company Codif, an extract of *Laminaria saccharina*, canola oil, bisabolol and camomile extracts, allantoin, Sepivital EPC (phosphoric diester of vitamin E and C) from SEPPIC, omega-3 unsaturated oils such as musk rose oil, blackcurrant oil, ecchium oil, fish oil, plankton extracts, capryloylglycine, Seppicalm VG (sodium palmitoylproline and *Nymphea alba*) from SEPPIC, an extract of *Pygeum*, an extract of *Boswellia serrata*, an extract of *Centipeda cunnighami*, an extract of *Helianthus annuus*, an extract of *Linum usitatissimum*, tocotrienols, extracts of *Cola nitida*, piperonal, an extract of clove, an extract of *Epilobium angustifolium*, aloe vera, an extract of *Bacopa moniera*, phytosterols, cortisone, hydrocortisone, indomethacin and betamethasone.

The calmatives are generally present in the composition used according to the invention in proportions ranging from 0.01 to 15% by weight, preferably ranging from 0.1 to 10% by weight, relative to the total weight of the composition.

The organic photoprotective agents are in particular chosen from anthranilates; cinnamic derivatives; dibenzoylmethane derivatives; salicylic derivatives, camphor derivatives; triazine derivatives such as those described in patent applications U.S. Pat. No. 4,367,390, EP863145, EP517104, EP570838, EP796851, EP775698, EP878469, EP933376, EP507691, EP507692, EP790243 and EP944624; benzophenone derivatives; β,β-diphenylacrylate derivatives; benzotriazole derivatives; benzalmalonate derivatives; benzimidazole derivatives; imidazolines; bis-benzoazolyl derivatives as described in patents EP669323 and U.S. Pat. No. 2,463,264; p-aminobenzoic acid (PABA) derivatives; methylenebis(hydroxyphenylbenzotriazole) derivatives as described in applications U.S. Pat. Nos. 5,237,071, 5,166, 355, GB2303549, DE19726184 and EP893119; screening polymers and screening silicones such as those described in particular in application WO-93/04665; and α-alkylstyrene-derived dimers such as those described in patent application DE 19855649.

The inorganic photoprotective agents can in particular be chosen from coated or uncoated metal oxide pigments or nanopigments (average size of the primary particles generally between 5 nm and 100 nm, preferably between 10 nm and 50 nm), for instance nanopigments of titanium oxide (amorphous or crystallized in rutile and/or anatase form), of iron oxide, of zinc oxide, of zirconium oxide or cerium oxide, which are all well-known UV photoprotective agents. Conventional coating agents are, moreover, alumina and/or aluminium stearate. Such coated or uncoated metal oxide nanopigments are in particular described in patent applications EP518772 and EP518773.

The photoprotective agents are generally present in the composition used according to the invention in proportions ranging from 0.1 to 20% by weight, preferably ranging from 0.2 to 15% by weight, relative to the total weight of the composition.

The composition used according to the invention may be in any of the galenical forms normally used in the cosmetics field, and in particular in the form of an optionally gelled aqueous or aqueous-alcoholic solution, a dispersion, optionally a two-phase dispersion, of the lotion type, an oil-in-water or water-in-oil or multiple (W/O/W or O/W/O) emulsion, an aqueous gel, a dispersion of oil in an aqueous phase by means of spherules, it being possible for these spherules to be polymeric nanoparticles such as nanospheres and nanocapsules or, better still, lipid vesicles of ionic and/or nonionic type; or aqueous or oily gels. These compositions are prepared according to the usual methods. According to this invention, a composition in the form of an emulsion, in particular an oil-in-water emulsion, is preferably used.

The composition used according to the invention may constitute a skincare composition, and in particular a cleansing, protecting, treatment or care cream for the face, for the hands, for the feet, for the major anatomical folds or for the body (for example, day creams, night creams, makeup-removing creams, foundation creams, antisun creams); a fluid foundation, a makeup-removing milk, a protective or care body milk or an antisun milk; a skincare lotion, gel or foam, such as a cleansing lotion.

The invention is illustrated in greater detail by the following nonlimiting examples.

EXAMPLES 1 to 4

Demonstration of the Activity on Constitutive Melanogenesis

A biological test demonstrated the depigmenting activity of 7 compounds of formula (I) (compounds 2, 7, 12, 16, 19, 21 and 27).

The modulatory effect of each compound on melanogenesis was measured according to the method described in FR-A-2734825 and also in the article by R. Schmidt, P. Krien and M. Regnier, Anal. Bichem., 235(2), 113-18,1996. This test is carried out on a coculture of keratinocytes and melanocytes.

For the compounds tested, the following were determined:
the cytotoxicity, by estimating leucine incorporation,
the inhibitory activity on melanin synthesis, by estimating the ratio of thiouracil incorporation to leucine incorporation, relative to 100% of the control (the control corresponds to the test carried out without test compound). The IC50 values (concentration for which 50% of the melanin synthesis is inhibited) were determined.

The test was also carried out with arbutin, niacinamide and kojic acid, which are known depigmenting compounds.

The results are collated in the following table:

| Compound | Cytotoxicity on coculture | IC50 |
|---|---|---|
| Arbutin | Non-cytotoxic | Not attained (or greater than 500 μM) |
| Kojic acid | 100 μM | Not attained (or greater than 500 μM) |
| Niacinamide | Non-cytotoxic | Not attained |
| Compound 2 | Non-cytotoxic | 4.9 μM |
| Compound 12 | Non-cytotoxic | 37 μM |
| Compound 16 | 100 μM | 25 μM |
| Compound 7 | Non-cytotoxic | 32 μM |
| Compound 27 | Non-cytotoxic | 29 μM |

-continued

| Compound | Cytotoxicity on coculture | IC50 |
|---|---|---|
| Compound 19 | Non-cytotoxic | 410 μM |
| Compound 21 | Non-cytotoxic | 128 μM |

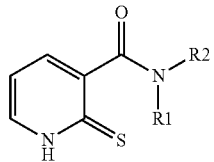

Compounds 2, 7, 12, 16, 19, 21 and 27 therefore demonstrate their efficacy in inhibiting melanogenesis and are, moreover, more effective than arbutin, kojic acid and niacinamide.

Compound 2 is the most effective compound.

EXAMPLE 5

A depigmenting gel for the skin is prepared, comprising (% by weight):

| | |
|---|---|
| Compound 2 | 2% |
| Carbomer (Carbopol 981 from Lubrizol) | 1% |
| preservative | qs |
| water | qs 100% |

When applied to the skin, the composition makes it possible to fade out brown marks.

A similar composition is prepared with compound 3 or compound 11 or compound 16.

The invention claimed is:

1. A depigmenting or lightening composition for at least one human keratin material selected from the group consisting of body skin of human beings, face skin of human beings, lips of human beings, and scalp of human beings, in a physiologically acceptable medium which is compatible with at least one of body skin of human beings, face skin of human beings, lips of human beings, and scalp of human beings, comprising from 0.1 to 10% by weight relative to the total weight of the composition of at least one compound of formula (Ia)

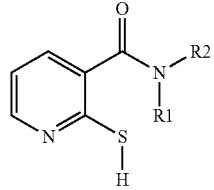

(Ia)

or its tautomeric form of formula (I'a)

(I'a)

wherein $R_1$ denotes a hydrogen atom or a saturated linear $C_1$-$C_{10}$ or branched $C_3$-$C_{10}$ or unsaturated $C_2$-$C_{10}$ alkyl group, optionally substituted with one or more —$OR_3$ groups, when $R_1$ denotes a hydrogen atom, then $R_2$ denotes a radical chosen from unsaturated $C_2$-$C_{20}$ alkyls, cyclic $C_7$ alkyl radicals, saturated linear $C_1$-$C_{20}$ alkyls optionally substituted with one or more identical or different —$OR_3$ groups, saturated branched $C_3$-$C_{20}$ alkyls optionally substituted with one or more identical or different —$OR_3$ groups, and ($C_1$-$C_{20}$)alkylaryls substituted with one or more identical or different —$OR_3$ groups, $R_3$ denoting a hydrogen atom or a saturated linear $C_1$-$C_5$ or branched $C_3$-$C_5$ or unsaturated $C_2$-$C_5$ group;

when $R_1$ denotes a saturated linear $C_1$-$C_{10}$ or branched $C_3$-$C_{10}$ or unsaturated $C_2$-$C_{10}$ alkyl group, optionally substituted with one or more —$OR_3$ groups, then $R_2$ denotes a radical chosen from a saturated branched $C_3$-$C_{12}$ or cyclic $C_3$-$C_7$ alkyl group, optionally interrupted with one or more oxygen atoms, and/or optionally containing one or more identical or different —$OR_3$ groups, and $R_3$ denotes a hydrogen atom or an optionally hydroxylated, saturated linear $C_1$-$C_5$ or branched $C_3$-$C_5$ hydrocarbon group, or a salt thereof, optical isomer thereof or racemate thereof, wherein the composition depigments or lightens a keratin material after application to the keratin material.

2. The composition of claim 1, wherein when $R_1$ denotes a hydrogen atom, then $R_2$ denotes a radical chosen from unsaturated $C_2$-$C_{20}$ alkyls, saturated linear $C_1$-$C_{20}$ alkyls optionally substituted with one or more identical or different —$OR_3$ groups, saturated branched $C_3$-$C_{20}$ alkyls optionally substituted with one or more identical or different —$OR_3$ groups, and ($C_1$-$C_6$)alkylphenyls substituted with one or more identical or different —$OR_3$ groups, $R_3$ denoting a hydrogen atom or a saturated linear $C_1$-$C_5$ or branched $C_3$-$C_5$ or unsaturated $C_2$-$C_5$ group;

when $R_1$ denotes a saturated linear $C_1$-$C_{10}$ or branched $C_3$-$C_{10}$ or unsaturated $C_2$-$C_{10}$ alkyl group, optionally substituted with one or more —$OR_3$ groups, then $R_2$ denotes a radical chosen from a saturated branched $C_3$-$C_{12}$ or cyclic $C_3$-$C_7$ alkyl group, optionally interrupted with one or more oxygen atoms, and/or optionally containing one or more identical or different —$OR_3$ groups, and $R_3$ denotes a hydrogen atom or an optionally hydroxylated, saturated linear $C_1$-$C_5$ or branched $C_3$-$C_5$ hydrocarbon group.

3. The composition of claim 1, wherein
when $R_1$ denotes a hydrogen atom, then $R_2$ denotes a radical chosen from saturated linear $C_1$-$C_{20}$ alkyls optionally substituted with one or more identical or different —$OR_3$ groups, saturated branched $C_3$-$C_{20}$ alkyls optionally substituted with one or more identical or different —$OR_3$ groups, and ($C_1$-$C_6$)alkylphenyls substituted with one or more identical or different —$OR_3$ groups, $R_3$ denoting a hydrogen atom or a saturated linear $C_1$-$C_5$ or branched $C_3$-$C_5$ or unsaturated $C_2$-$C_5$ group;
when $R_1$ denotes a saturated linear $C_1$-$C_{10}$ or branched $C_3$-$C_{10}$ or unsaturated $C_2$-$C_{10}$ alkyl group, optionally substituted with one or more —$OR_3$ groups, then $R_2$ denotes a radical chosen from
a saturated branched $C_3$-$C_{12}$ or cyclic $C_3$-$C_7$ alkyl group, optionally interrupted with one or more oxygen atoms, and/or optionally containing one or more identical or different —$OR_3$ groups, and
$R_3$ denotes a hydrogen atom or an optionally hydroxylated, saturated linear $C_1$-$C_5$ or branched $C_3$-$C_5$ hydrocarbon group.

4. The composition of claim 1, wherein the compound is
N-(2-hydroxyethyl)-2-thioxo-1,2-dihydropyridine-3-carboxamide;
N,N-bis(2-hydroxyethyl)-2-thioxo-1,2-dihydropyridine-3-carboxamide;
N-(2,3-dihydroxypropyl)-2-thioxo-1,2-dihydropyridine-3-carboxamide;
N-(1,3-dihydroxypropan-2-yl)-2-thioxo-1,2-dihydropyridine-3-carboxamide;
N-(1,3-dihydroxypropan-2-yl)-2-thioxo-1,2-dihydropyridine-3-carboxamide;
N-ethyl-N-(2-hydroxyethyl)-2-thioxo-1,2-dihydropyridine-3-carboxamide; or
N-[2-(2-hydroxyethoxy)ethyl]-2-thioxo-1,2-dihydropyridine-3-carboxamide.

5. The composition of claim 1, wherein $R_1$ denotes a hydrogen atom.

6. The composition of claim 1, wherein $R_1$ denotes a saturated linear $C_1$-$C_{10}$ or branched $C_3$-$C_{10}$ or unsaturated $C_2$-$C_{10}$ alkyl group, optionally substituted with one or more —$OR_3$ groups.

7. The composition of claim 1, wherein the physiologically acceptable medium is compatible with body skin of human beings.

8. The composition of claim 1, wherein the physiologically acceptable medium is compatible with lips of human beings.

9. The composition of claim 1, wherein the compound is N-ethyl-N-(2-hydroxyethyl)-2-thioxo-1,2-dihydropyridine-3-carboxamide.

10. The composition of claim 1, wherein the composition comprises from 0.5 to 5% by weight relative to the total weight of the composition of at least one compound of formula (Ia).

11. The composition of claim 1, wherein the composition comprises from 0.5 to 3% by weight relative to the total weight of the composition of at least one compound of formula (Ia).

12. The composition of claim 1, which comprises 0.1 to 5% by weight of the compound of formula (Ia) or its tautomeric form of formula (I'a).

13. The composition of claim 12, wherein
when $R_1$ denotes a hydrogen atom, then $R_2$ denotes a radical chosen from unsaturated $C_2$-$C_{20}$ alkyls, saturated linear $C_1$-$C_{20}$ alkyls optionally substituted with one or more identical or different —$OR_3$ groups, saturated, branched $C_3$-$C_{20}$ alkyls optionally substituted with one or more identical or different —$OR_3$ groups, and ($C_1$-$C_6$)alkylphenyls substituted with one or more identical or different —$OR_3$ groups, $R_3$ denoting a hydrogen atom or a saturated linear $C_1$-$C_5$ or branched $C_3$-$C_5$ or unsaturated $C_2$-$C_5$ group;
when $R_1$ denotes a saturated linear $C_1$-$C_{10}$ or branched $C_3$-$C_{10}$ or unsaturated $C_2$-$C_{10}$ alkyl group, optionally substituted with one or more —$OR_3$ groups, then $R_2$ denotes a radical chosen from
a saturated branched $C_3$-$C_{12}$ or cyclic $C_3$-$C_7$ alkyl group, optionally interrupted with one or more oxygen atoms, and/or optionally containing one or more identical or different —$OR_3$ groups, and
$R_3$ denotes a hydrogen atom or an optionally hydroxylated, saturated linear $C_1$-$C_5$ or branched $C_3$-$C_5$ hydrocarbon group.

14. The composition of claim 12, wherein
when $R_1$ denotes a hydrogen atom, then $R_2$ denotes a radical chosen from saturated linear $C_1$-$C_{20}$ alkyls optionally substituted with one or more identical or different —$OR_3$ groups, saturated branched $C_3$-$C_{20}$ alkyls optionally substituted with one or more identical or different —$OR_3$ groups, and ($C_1$-$C_6$)alkylphenyls substituted with one or more identical or different —$OR_3$ groups, $R_3$ denoting a hydrogen atom or a saturated linear $C_1$-$C_5$ or branched $C_3$-$C_5$ or unsaturated $C_2$-$C_5$ group;
when $R_1$ denotes a saturated linear $C_1$-$C_{10}$ or branched $C_3$-$C_{10}$ or unsaturated $C_2$-$C_{10}$ alkyl group, optionally substituted with one or more —$OR_3$ groups, then $R_2$ denotes a radical chosen from
a saturated branched $C_3$-$C_{12}$ or cyclic $C_3$-$C_7$ alkyl group, optionally interrupted with one or more oxygen atoms, and/or optionally containing one or more identical or different —$OR_3$ groups, and
$R_3$ denotes a hydrogen atom or an optionally hydroxylated, saturated linear $C_1$-$C_5$ or branched $C_3$-$C_5$ hydrocarbon group.

15. The composition of claim 12, wherein the compound is
N-(2-hydroxyethyl)-2-thioxo-1,2-dihydropyridine-3-carboxamide;
N,N-bis(2-hydroxyethyl)-2-thioxo-1,2-dihydropyridine-3-carboxamide;
N-(2,3-dihydroxypropyl)-2-thioxo-1,2-dihydropyridine-3-carboxamide;
N-(1,3-dihydroxypropan-2-yl)-2-thioxo-1,2-dihydropyridine-3-carboxamide;
N-(1,3-dihydroxypropan-2-yl)-2-thioxo-1,2-dihydropyridine-3-carboxamide;
N-ethyl-N-(2-hydroxyethyl)-2-thioxo-1,2-dihydropyridine-3-carboxamide; or
N-[2-(2-hydroxyethoxy)ethyl]-2-thioxo-1,2-dihydropyridine-3-carboxamide.

16. The composition of claim 12, wherein $R_1$ denotes a hydrogen atom.

17. The composition of claim 12, wherein $R_1$ denotes a saturated linear $C_1$-$C_{10}$ or branched $C_3$-$C_{10}$ or unsaturated $C_2$-$C_{10}$ alkyl group, optionally substituted with one or more —$OR_3$ groups.

18. The composition of claim 12, wherein the physiologically acceptable medium is compatible with body skin of human beings.

19. The composition of claim 12, wherein the physiologically acceptable medium is compatible with lips of human beings.

20. The composition of claim 12, wherein the compound is N-ethyl-N-(2-hydroxyethyl)-2-thioxo-1,2-dihydropyridine-3-carboxamide.

* * * * *